(12) United States Patent
Barlow et al.

(10) Patent No.: US 11,096,619 B2
(45) Date of Patent: Aug. 24, 2021

(54) NEURAL ANALYSIS AND TREATMENT SYSTEM

(71) Applicant: Innara Health, Olathe, KS (US)

(72) Inventors: Steven M. Barlow, Lawrence, KS (US); David L. Stalling, Olathe, KS (US); Kenneth Aron, Olathe, KS (US)

(73) Assignee: Innara Health, Inc., Olathe, KS (US)

( * ) Notice: Subject to any disclaimer, the term of this patent is extended or adjusted under 35 U.S.C. 154(b) by 928 days.

(21) Appl. No.: 14/330,712

(22) Filed: Jul. 14, 2014

(65) Prior Publication Data

US 2015/0018705 A1  Jan. 15, 2015

Related U.S. Application Data

(60) Provisional application No. 61/845,842, filed on Jul. 12, 2013, provisional application No. 61/872,236, filed on Aug. 30, 2013.

(51) Int. Cl.
*A61B 5/00* (2006.01)
*A61B 5/383* (2021.01)
*A61B 5/377* (2021.01)
*A61B 5/374* (2021.01)

(52) U.S. Cl.
CPC .............. *A61B 5/377* (2021.01); *A61B 5/374* (2021.01); *A61B 5/7242* (2013.01); *A61B 2503/045* (2013.01)

(58) Field of Classification Search
None
See application file for complete search history.

(56) References Cited

U.S. PATENT DOCUMENTS

| | | | | |
|---|---|---|---|---|
| 8,190,249 | B1* | 5/2012 | Gharieb | A61B 5/0402 600/508 |
| 2003/0013981 | A1* | 1/2003 | Gevins | A61B 5/0484 600/544 |
| 2004/0059241 | A1* | 3/2004 | Suffin | A61B 5/0006 600/544 |
| 2006/0009709 | A1* | 1/2006 | Rautee | A61B 5/4076 600/544 |

(Continued)

FOREIGN PATENT DOCUMENTS

WO  WO-2013060788 A2 *  5/2013 ........... G01N 27/447

OTHER PUBLICATIONS

O'Reilly et al. Peak-to-peak amplitude in neonatal brain monitoring of premature infants. Clinical Neurophysiology 123 (2012) 2139-2153.*

(Continued)

*Primary Examiner* — Etsub D Berhanu
(74) *Attorney, Agent, or Firm* — Polsinelli PC

(57) ABSTRACT

A neural analysis and treatment system includes a computing device with a memory for storing an application that is executable on a processor to receive amplitude-integrated electroencephalography (aEEG) and range-EEG (rEEG) measurements associated with a patient. The systems determine a spectral edge frequency (SEF) measurement from the received EEG measurements, and determine one or more neural characteristics of the patient according to the determined SEF, aEEG, and rEEG measurements. These neural characteristics may then be used to identify and implement an appropriate therapeutic treatment.

27 Claims, 11 Drawing Sheets

(56) References Cited

U.S. PATENT DOCUMENTS

| | | | | |
|---|---|---|---|---|
| 2008/0027348 A1* | 1/2008 | Harris | ............... | A61B 5/0031 |
| | | | | 600/545 |
| 2008/0033502 A1* | 2/2008 | Harris | ............... | A61B 5/0031 |
| | | | | 607/45 |
| 2009/0018462 A1* | 1/2009 | Bell | ............... | A61B 5/02405 |
| | | | | 600/544 |
| 2010/0075285 A1* | 3/2010 | Stalling | ............ | A63B 23/032 |
| | | | | 434/258 |
| 2010/0286549 A1* | 11/2010 | John | ............... | A61B 5/0476 |
| | | | | 600/544 |

OTHER PUBLICATIONS

Inder et al. Lowered Electroencephalographic Spectral Edge Frequency Predicts the Presence of Cerebral White Matter Injury in Premature Infants. Pediatrics, Jan. 2003, vol. 111/Issue 1.*

Song et al. Modulation of EEG spectral edge frequency during patterned pneumatic oral stimulation in preterm infants. Pediatric Research (2014) 75, 85-92.*

Niemarkt et al. Maturational Changes in Automated EEG Spectral Power Analysis in Preterm Infants. Pediatrics Research (2011) vol. 70, No. 5.*

* cited by examiner

| PERIODS | P1 | P2 | P3 | P4 | P5 | P6 | P7 | P8 | P9 |
|---|---|---|---|---|---|---|---|---|---|
| NT Stim | Base | Base | [1] | OUT | [1] | OUT | [1] | Post | Post |
| Blind Pacifier | Base | Base | [2] | OUT | [2] | OUT | [2] | Post | Post |
| DURATION | 3 min | 3 min | 3 min | 5.5 min | 3 min | 5.5 min | 3 min | 3 min | 3 min |
| | | | \multicolumn{5}{c}{NG Feed plus [1] pneumatically-charged Philips AVANT Soothie® silicone pacifier, or a [2] blind Soothie® pacifier} | | | |

Fig. 10A

| Variable | Bonferroni-adjusted p | | | | | |
|---|---|---|---|---|---|---|
| | G1 - G2 | G1 - G3 | G1 - G4 | G2 - G3 | G2 - G4 | G3 - G4 |
| aEEG max left | 0.246 | 0.000 | 0.000 | 0.000 | 0.000 | 0.056 |
| aEEG mean left | 1.000 | 0.000 | 0.000 | 0.000 | 0.000 | 0.714 |
| aEEG min left | 1.000 | 0.000 | 0.000 | 0.000 | 0.000 | 1.000 |
| aEEG max right | 0.683 | 0.098 | 0.076 | 0.002 | 0.785 | 0.000 |
| aEEG mean right | 1.000 | 0.862 | 0.803 | 0.297 | 0.789 | 0.011 |
| aEEG min right | 1.000 | 1.000 | 1.000 | 1.000 | 0.870 | 1.000 |
| aEEG max xhead | 0.004 | 0.000 | 0.000 | 1.000 | 0.000 | 0.000 |
| aEEG mean xhead | 0.404 | 1.000 | 0.001 | 0.204 | 0.025 | 0.000 |
| aEEG min xhead | 1.000 | 0.150 | 0.433 | 0.370 | 1.000 | 1.000 |
| BAND A left | 0.000 | 1.000 | 0.061 | 1.000 | 1.000 | 1.000 |
| BAND B left | 0.004 | 0.000 | 0.000 | 1.000 | 0.064 | 1.000 |
| BAND C left | 0.000 | 0.000 | 0.000 | 0.000 | 0.000 | 0.000 |
| BAND D left | 0.469 | 0.000 | 0.000 | 0.000 | 0.000 | 0.000 |
| BAND E left | 0.000 | 0.000 | 0.000 | 0.535 | 0.000 | 1.000 |
| BAND A right | 1.000 | 0.299 | 1.000 | 0.836 | 0.348 | 1.000 |
| BAND B right | 1.000 | 0.410 | 1.000 | 1.000 | 0.000 | 0.397 |
| BAND C right | 1.000 | 0.000 | 0.000 | 0.467 | 0.000 | 0.000 |
| BAND D right | 1.000 | 0.149 | 1.000 | 0.024 | 0.000 | 1.000 |
| BAND E right | 0.000 | 0.000 | 0.000 | 0.000 | 0.010 | 0.000 |
| BAND A total | 0.021 | 1.000 | 0.015 | 1.000 | 1.000 | 1.000 |
| BAND B total | 1.000 | 1.000 | 1.000 | 1.000 | 1.000 | 1.000 |
| BAND C total | 1.000 | 0.000 | 1.000 | 0.000 | 0.000 | 0.004 |
| BAND D total | 0.000 | 0.000 | 0.000 | 0.000 | 0.014 | 0.000 |
| BAND E total | 0.000 | 0.000 | 0.000 | 1.000 | 0.000 | 0.000 |

Fig. 10B

NEURAL ANALYSIS AND TREATMENT SYSTEM

RELATED APPLICATIONS

This application claims priority to U.S. Provisional Patent Application No. 61/845,842, filed on Jul. 12, 2013, entitled "Neural Analysis and Treatment System," and U.S. Provisional Patent Application No. 61/872,236, filed on Aug. 30, 2013, also entitled "Neural Analysis and Treatment System", the contents of each provisional application including all appendices, is herein incorporated by reference in its entirety.

FEDERALLY SPONSORED RESEARCH OR DEVELOPMENT

The subject matter discussed in this patent application was funded in part by United States Grant No. RO1 DC003311 from the National Institute of Health (NIH). The government may have certain rights to the subject matter discussed herein.

COMPACT DISK APPENDIX

Not Applicable.

FIELD OF INVENTION

The present invention generally relates to diagnostic and therapeutic systems, devices, and methods. In particular, the present invention relates to a neural analysis and treatment system.

BACKGROUND

The infant brain is a developing organ of enormous complexity, whose initial form is specified through genetic instruction. It has been shown that pathway formation and network tuning are subsequently modified and continuously refined by experience and activity-dependent mechanisms. For the premature infant, extrauterine life is a pathological condition, and defining normality of electrocortical activity represents a significant challenge in the neonatal intensive care unit.

To address this challenge, reduced-montage electroencephalography is currently used to monitor and map brain maturation and assess neurological status in preterm infants. Therefore, what is needed is a system that provides for enhanced analysis and treatment of preterm infants as well as other types of patients having neural disorders.

SUMMARY

Embodiments of the neural analysis and treatment system may provide a solution to conventional EEG systems using a combination of amplitude-integrated electroencephalography (aEEG) as well as range-electroencephalography (rEEG) information to determine one or more neural characteristics of a patient. In particular, the neural analysis and treatment system determines certain characteristics of preterm infants that may be used to alter cortical activity of the infant, quantify a spectral edge frequency (SEF) modulation in the EEG spectra, quantify the SEF asymmetry for diagnostic purposes, and quantify and promote cortical adaption.

According to one embodiment, a neural analysis and treatment system includes a computing device with a memory for storing an application that is executable on a processor to receive aEEG and rEEG measurements associated with a patient, determine a spectral edge frequency (SEF) measurement from the received EEG measurements, and determine one or more neural characteristics of the patient according to the determined SEF measurement.

BRIEF DESCRIPTION OF THE DRAWINGS

FIGS. 10A and 10B illustrate mixed model adjusted means, and Post-hoc pairwise comparison. G1: NT 'On' and Level 3,5,7; G2: NT 'On' and Level 1,2,4,6,8,9; G3: NT 'Off' and Level 3,5,7; and G4: NT 'Off' and Level 1,2,4,5,8,9, respectively according to one aspect of the present disclosure.

DETAILED DESCRIPTION

Figure 1A:
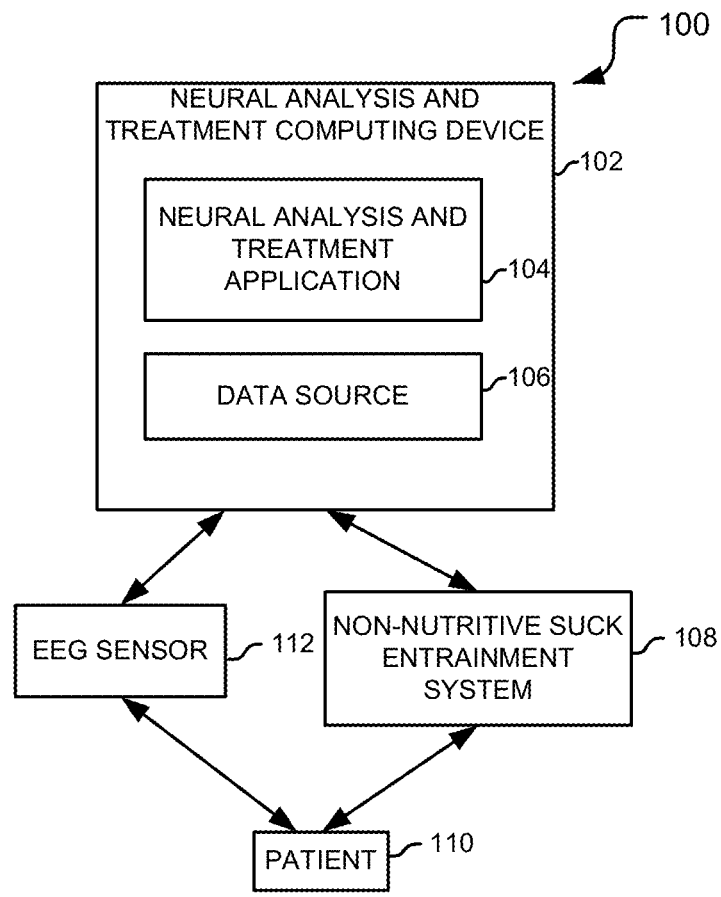
FIG. 1A is a block diagram of a computing system that includes a neural analysis and treatment system.

The amplitude-integrated electroencephalogram (aEEG), also known as the cerebral function monitor (CFM), reflects integrated brain activity and permits time-compressed, continuous bedside electrocortical monitoring. The dual-channel aEEG is typically recorded from two pairs of surface electrodes (e.g., C3-P3, C4-P4) situated on the scalp over the frontoparietal cortices, and proximal to forelimb and orofacial sensorimotor cortical representations. The aEEG can be recorded in newborns at all maturational levels, including extremely preterm infants (e.g., from 28 weeks of gestation), and the electrode montage may be left in position over relatively long periods encompassing hours or days.

The main features extracted from the aEEG include type of background activity, such as discontinuous/continuous activity, interburst intervals or burst rate, cyclic variation in the background activity corresponding to sleep-wake cycling (SWC), upper and lower amplitude margins, amplitude bandwidth, spectral composition, and the presence of seizure patterns.

In numerous studies, aEEG measurements have been increasingly used in monitoring brain activity of preterm infants. The aEEG measurements have also provided normative data on brain maturation in preterm infants at various gestational age (GA) and postmenstrual age (PMA). These studies have shown that neural characteristics, including but not limited to aEEG characteristics in preterm infants, including voltages, continuity, and sleep-wake cycling, mature with increasing GA and PMA. For example, with greater GA the relative amount of continuous activity (e.g., aEEG measurements greater than 5.0 microvolts ($\mu$V) and maximal amplitude between 20 and 40 microvolts ($\mu$V)) tends to increase while discontinuous patterns decrease. The number of bursts per hour decreased with increasing GA. In preterm infants with no evidence of brain abnormalities or injury, aEEG characteristics mature predominantly with PMA. For example, sleep state differentiation appears in neurologically normal infants at 27-29 weeks PMA. The presence of sleep-wake cycling in preterm infants is strongly associated with good long-term prognosis and is absent in most infants with severe intraventricular hemorrhage (IVH). Long-term outcome can be predicted by aEEG/EEG with 75-80% accuracy at 24 postnatal hours in very preterm infants (e.g., 28 to 32 weeks GA), and in infants with no early indication of brain injury.

Nevertheless, as the utility and scope of aEEG evolves, so does the need for quantitative normal values and standardized signal processing methods. For example, in one particular experiment, reference values of aEEG amplitude margins were obtained for 274 infants with a wide range of PMAs and constituted the basis for the quantitative assessment of aEEG changes with maturation in neonates and young infants. The upper and lower margins of the aEEG in both active and quiet sleep rose in infants after the neonatal period, while the bandwidth defined as a voltage distance between the upper and lower margins of the aEEG decreased monotonically throughout the PMA range from 30 to 55 weeks.

To date, nearly all studies of preterm brain cortical activity using aEEG/rEEG have been designed to map developmental features of maturation (e.g., continuity, amplitude margins, amplitude bands, and the like) and/or pathologic brain activity (e.g., seizures, discontinuity, and the like). However, it should be recognized that stimulation of the nervous system plays an important role in brain development and neurodevelopmental outcome. For example, brief, tactile stimulation can be applied to the hand (palm) and foot (sole) to evoke EEG and aEEG activity in extremely low birth weight infants (e.g., infants 24-28 weeks GA with EEG recorded at 30-32 weeks PMA). Additionally, an infant can be instrumented for aEEG and receive, on average, 17 minutes of whole body massage therapy performed 30 minutes after feeding. The amplitude of the aEEG trend significantly increased during massage, and also increased the dominant frequency 6 waves which returned to baseline after treatment.

The spectral signature of brain activity, including exogenous and autogenic frequency modulation (i.e., neonate state changes, external stimulation) and rhythmic electrocortical activity (resting state network dynamics) provides the clinician and neuroscientist with a window into the integrity and maturation of the human nervous system in the frequency domain. Spectral measures extracted from the EEG reflect complex processes related to cerebral and subcortical maturation and activity and experience dependent change. Subcortical inputs from brainstem and thalamus provide an essential source of patterned activity to the developing neocortex. It is thought that disruption of the thalamocortical system, correlated in EEG progression, represents a major component of preterm brain injury. Spectral measures have found application in identifying brain pathology. For example, spectral power of low frequencies (6 waves; 0-4 Hz) differs significantly between burst episodes of healthy and asphyxiated infants, and has been negatively correlated to the degree of white matter injury on MRI in premature infants. Diffusion tensor imaging (DTI) revealed that thalamocortical connectivity (between thalamus and frontal cortices, supplementary motor areas, occipital lobe, and temporal gyri) is significantly diminished in preterm infants. The anatomical findings were corroborated by hemodynamic measures of functional connectivity (fcMRI) showing that very preterm infants scanned at term equivalent age exhibit reduced connectivity between cerebral cortex and thalamus relative to full-term controls.

The effects of prematurity on the thalamocortical system negatively impacts neurodevelopmental outcome. In neurotypical infants, resting cortical activity is characterized by a distinct spectral peak in the alpha frequency range (8-13 Hz). Slowing of this oscillatory peak toward the upper theta-band (6-8 Hz) has been associated with a variety of neurological and neuropsychiatric conditions, and is attributed to altered thalamocortical dynamics. The importance of thalamic input on the generation of cortical oscillatory activity is of high importance for cognitive and perceptual processing. In a recent study, magnetoencephalography (MEG) was used to measure global spectral activity in 11 school-age children (approximately 7.5 years of age) born very preterm (less than 32 weeks gestation) without major intellectual or neurological impairment, and these children were compared to a group of 11 age-matched full-term controls. The very preterm children exhibited a slowing of peak frequency toward the theta-band over bilateral frontal cortex and a reduction in alpha-band power over bilateral frontal and temporal cortex. It is suggested that mildly dysrhythmic thalamocortical interactions may contribute to altered spontaneous cortical activity in children born very preterm.

Figure 1B:
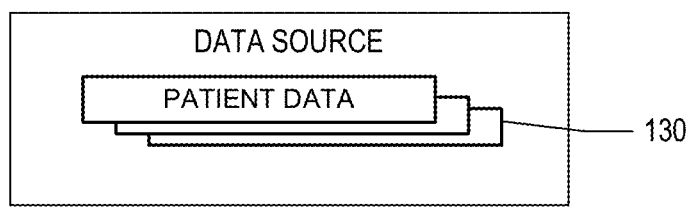
FIG. 1B depicts an exemplary embodiment of a computing device according to one aspect of the neural analysis and treatment system.

FIGS. 1A and 1B depict an example neural analysis and treatment system 100 according to aspects of the disclosure. The system 100 includes a neural analysis and treatment computing device 102 or other computing device or system that includes a neural analysis and treatment application 104 and a data source 106. As will be described in detail below, the application 104 receives aEEG and rEEG measurements of a patient 110, such as from an EEG sensor 112, and processes the aEEG and rEEG measurements to generate enhanced diagnostics for the patient 110. Optionally, the application 104 uses the generated diagnostics to develop a therapeutic plan, which may be, for example, a non-nutritive suck entrainment system (NNS) 108 that provides therapeutic stimulus to the patient.

According to the teachings of the present disclosure, a range-EEG (rEEG) value, which is calculated as the difference between maximum and minimum values for adjacent 2-second intervals from the raw EEG signal, may be used in conjunction with aEEG values for enhanced analysis of standardized normal assessments. Compared to aEEG, the rEEG represents a less conservative estimate of peak-to-peak amplitude derived from raw EEG.

In one embodiment, the system 100 provides a method for altering cortical activity. In another embodiment, the system 100 provides a method for quantifying the SEF modulation in the EEG spectra for diagnostic uses. In yet another embodiment, the system 100 provides a method of quantifying SEF asymmetry for diagnostic purposes. In yet another embodiment, the system 100 provides a method to quantify and promote cortical adaptation. Each of these features of the system 100 will be described in detail herein below.

In one particular embodiment, the rEEG-values are determined for each 2-second interval, linearly connected, and resampled at 8 Hz to provide a continuous signal using the same frequency that is used for storing and displaying aEEG on a BRM3 monitor or equivalent cribside EEG monitoring system (Natus NicONE monitor). Based on rEEG results, five amplitude bands that are designated A through E, are calculated to reflect the relative contribution of different rEEG values. In one embodiment, the boundaries for the five amplitude bands include A [0-10 microvolts], B [10-25 microvolts], C [25-50 microvolts], D [50-100 microvolts], and E [greater than 100 microvolts], and are expressed as the percentage of time each amplitude band appeared in a given 1 minute epoch (See FIG. 8). In one particular study, peak-to-peak amplitude (ppA) measures of aEEG and rEEG assessed in 26 extremely preterm infants were strongly associated with PMA, with rEEG showing more distinct patterns. There was a tendency for the representation of low voltages to increase while higher voltages decreased with increasing PMA, accompanied by a prominent increase in rEEG band C. This experiment demonstrates that the variance of log-transformed voltages are correlated with PMA ($R2=0.84-0.89$), exceeding previous correlations for the lower margin amplitude during quiet sleep ($R2=0.75$). The rEEG provides a relatively more precise estimate of peak-to-peak amplitude based on the raw EEG tracing when compared with aEEG, correlates strongly with PMA, and may serve as a biomarker for brain maturation and quantification of EEG suppression in brain injury. Incorporating both aEEG and rEEG offer the potential to advance an understanding of brain activity in health and disease among extremely premature infants.

Figure 2:
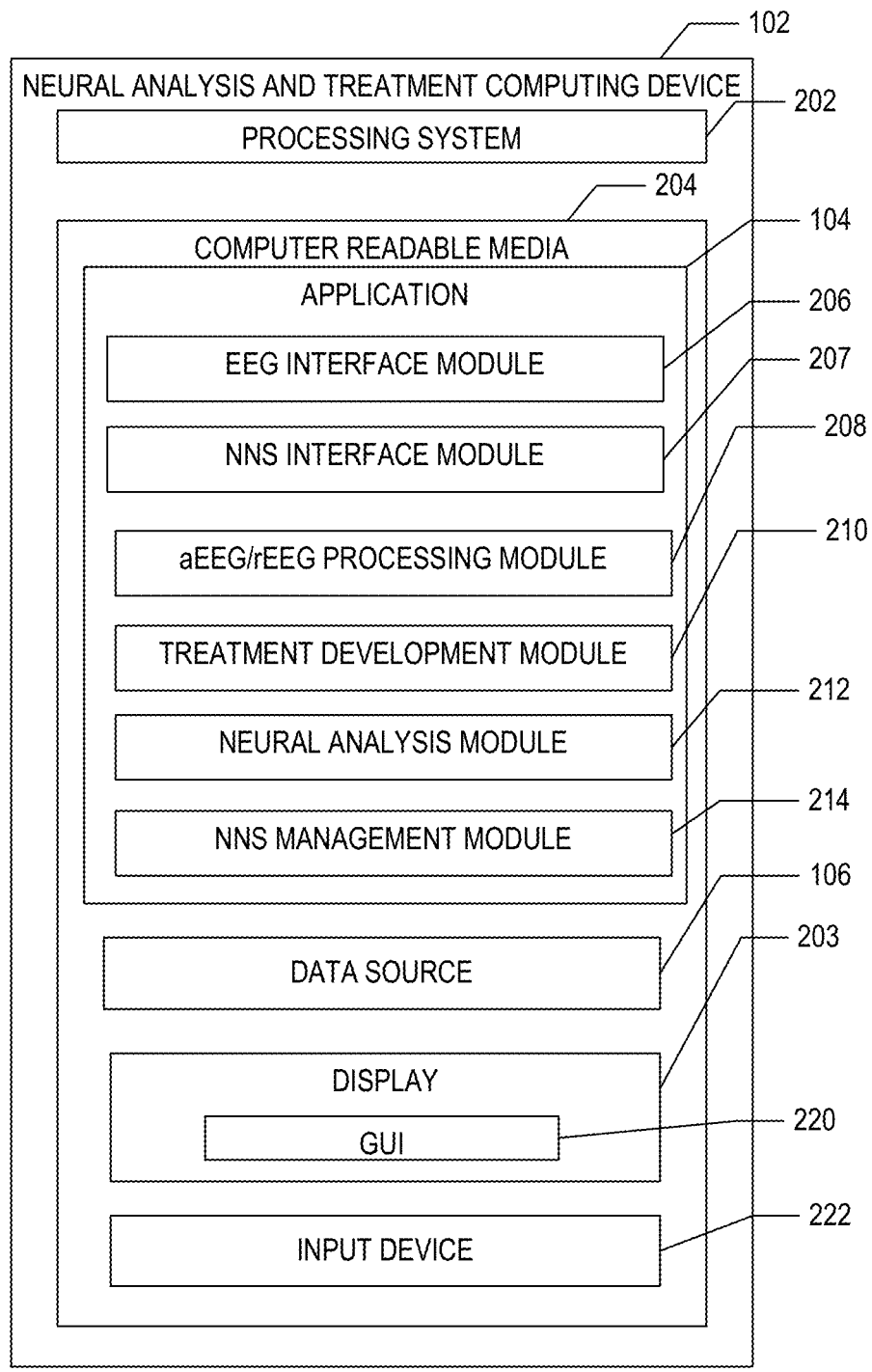
FIG. 2 is a block diagram of an example computing device that includes a neural analysis and treatment system.

In one embodiment, the computing device 102 includes a processing system 202, as shown in FIG. 2, that executes the neural analysis and treatment application 104 stored in volatile and/or non-volatile memory 204 (i.e., computer readable media) using the data source 106. Examples of such a computing device 102 includes one or more servers, personal computers, mobile computers and/or other mobile devices, and other computing devices. The computing device 102 may communicate via wireless and/or wireline communications.

The data source 106 stores patient data 130 including information associated with the patient. Although the data source 106 is shown as being located on, at, or within the computing device 102, it is contemplated that the data source 106 can be located remotely from the computing device 102 in other aspects of the system 100, such as on, at, or within a database of a data management system or a database of another computing device or system having at least one processor and volatile and/or non-volatile memory.

FIG. 2 also provides a block diagram of an embodiment of a neural analysis and treatment application 104 that can be executed on the computing device 102. According to one aspect, the neural analysis and treatment computing device 102 includes a processing system 202 that includes one or more processors or other processing devices. A processor is hardware. The processing system 202 executes the neural analysis and treatment application 104 to provide one or more neural analysis and/or entrainment procedures, such as altering cortical activity, quantifying and promoting cortical adaptation of the patient, quantifying SEF modulation in the EEG spectra for diagnostic uses, and/or quantifying SEF asymmetry for diagnostic purposes.

The neural analysis and treatment computing device 102 includes a computer readable media 204 on which the neural analysis and treatment application 104 and data source 106 are stored. The neural analysis and treatment application 104 includes instructions or modules that are executable by the processing system 202 to perform the features of the application 104 described herein.

The computer readable media 204 may include volatile media, nonvolatile media, removable media, non-removable media, and/or another available media that can be accessed by the neural analysis and treatment computing device 102. By way of example and not limitation, computer readable media 204 comprises computer storage media and communication media. Computer storage media includes non-transient storage memory/media, volatile media, nonvolatile media, removable media, and/or non-removable media implemented in a method or technology for storage of information, such as computer/machine readable/executable instructions, data structures, program modules, and/or other data. Communication media may embody computer readable instructions, data structures, program modules, or other data and include an information delivery media or system.

An EEG interface module 206 receives patient information about the patient 110, such as aEEG and rEEG information associated with the patient's brainwaves. In one embodiment, the EEG sensor 112 includes its own computing device such that the EEG interface module 206 communicates with the EEG sensor 112 via wireless and/or wireline communications. That is, the computing device of the EEG sensor 112 may have one or more processors and volatile and/or non-volatile memory. Examples of such a remote computing device may include one or more personal computers, mobile computers and/or other mobile devices, and other computing devices. In another embodiment, the EEG interface module 206 may receive patient information directly using telemetry information from sensors configured in the NNS entrainment system 108 or a module thereof.

An NNS entrainment system interface module 207 communicates with the NNS entrainment system 108 to assess and entrain brain activity for controlling respiration, mastication, or other neuromuscular functions of the patient. Additional details related to the NNS entrainment system 108 are disclosed in U.S. patent application Ser. No. 13/457,059, entitled "Enhanced therapeutic stimulus system and methods of use," filed Apr. 26, 2012; U.S. patent application Ser. No. 13/457,203, entitled "Enhanced Therapeutic Stimulus For Non-Nutritive Suck Entrainment System and Method," filed Apr. 26, 2012; and U.S. patent application Ser. No. 13/457,154, entitled "Methods of Using An Enhanced Therapeutic Stimulus for Non-Nutritive Suck Entrainment System," filed Apr. 26, 2012; each of which is incorporated herein by reference in its entirety. Although the aEEG/rEEG analysis system is described herein for use with an NNS device or the NNS entrainment system 108, it should be understood that that the aEEG/rEEG analysis system may be used with any other system that performs a therapeutic plan on the patient using processed EEG data.

An aEEG/rEEG processing module 208 generates aEEG and rEEG information from patient information gathered by the EEG interface module 206. In one embodiment, the aEEG/rEEG processing module 208 generates the aEEG and rEEG information from raw EEG data obtained from the EEG interface module 206. In another embodiment, the aEEG/rEEG processing module 208 processes aEEG/rEEG information generated by the EEG sensor 112.

A treatment development module 210 develops a therapeutic plan to be used by the NNS entrainment system 108 for correcting and otherwise alleviating an abnormality of the patient 110. For example, the treatment development module 210 develops an entrainment procedure for training certain brainwave behavior in the patient. In another example, the treatment development module 210 may develop a therapeutic plan or protocol to alter cortical activity of the patient 110. In another example, the treatment development module 210 may develop a therapeutic plan to quantify and promote cortical adaptation of the patient.

A neural analysis module 212 generates one or more reports that may be used by personnel, including researchers and healthcare providers, among others, for determining one or more conditions associated with the patient 110. For example, the neural analysis module 212 may quantify SEF modulation in the EEG spectra of the received aEEG/rEEG information for diagnostic uses. As another example, the neural analysis module 212 may quantify SEF asymmetry of the aEEG/rEEG information for diagnostic purposes.

A NNS management module 214 manages the overall operation of the NNS entrainment system 108. For example, the NNS management module 214 generates a graphical user interface (GUI) 220 that displays various activities and provides for administrative control of the NNS entrainment system 108 from the neural analysis and treatment computing device 102. For example, the GUI 220 may display operating characteristics of the NNS entrainment system 108 and receive user input via an input device 222 for controlling the operation of the NNS entrainment system 108.

It should be appreciated that the modules described herein are provided only as an example of a computing device that may execute the neural analysis and treatment application 104 according to the teachings of the present invention, and that other computing devices may have the same modules, different modules, additional modules, or fewer modules than those described herein. For example, one or more modules as described in FIG. 2 may be combined into a single module. As another example, certain modules described herein may be encoded and executed on other computing devices, such as the computing device configured in the NNS entrainment system 108. Additionally, one or more of the modules may be stored and executed by the neural analysis and treatment computing device 102, where data and instructions are transmitted to and from the neural analysis and treatment computing device 102 and the computing device of the NNS entrainment system 108 to execute their functions.

Figure 3:
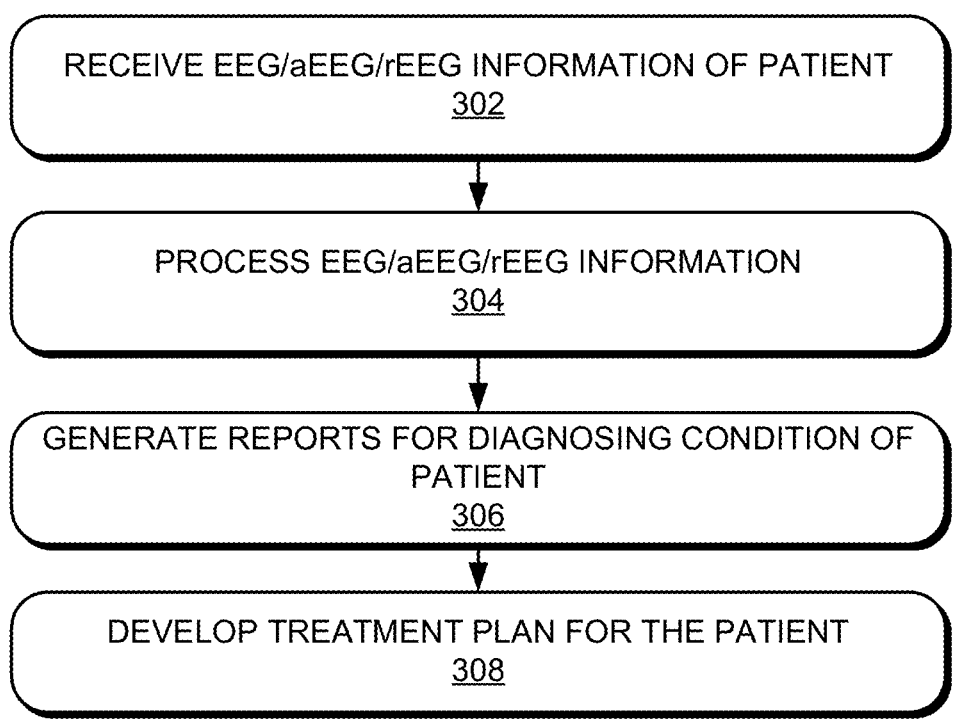
FIG. 3 is a flowchart depicting a process that may be performed by the neural analysis and treatment application according to an aspect of the neural analysis and treatment system.

FIG. 3 illustrates an example process that may be performed by the neural analysis and treatment application 104 according to the teachings of the present disclosure.

In step 302, the application 104 receives EEG/aEEG/rEEG information associated with a patient. The EEG/aEEG/rEEG information may be obtained from any suitable source, such as an EEG sensor that obtains aEEG/rEEG information of a preterm infant. In one embodiment, the neural analysis and treatment application 104 generates the aEEG and rEEG information from raw EEG data obtained from the EEG sensor 112. In another embodiment, the neural analysis and treatment application 104 processes aEEG/rEEG information that has been generated by the EEG sensor 112.

In step 304, the application 104 processes the received EEG information. In one embodiment, the application 104 generates spectral edge frequency (SEF) information from the received EEG/aEEG/rEEG information. Spectral edge frequency, typically expressed as SEF-"X," identifies the frequency below which "X" percent of the total power of a given signal is located. For example, SEF-90 is defined as the frequency below which 90% of the power in a spectrum resides. In many cases, SEF-90 measurements are thought to reflect cerebral maturation. The observed modulation in the EEG spectra during and after somatosensory stimulation is a reflection of the dynamics of thalamocortical excitation resulting from synchronous volleys of oral mechanoreceptive afferent activity in the maxillary (V2) and mandibular (V3) divisions of the trigeminal nerve evoked by the pulsed pneumatic orocutaneous stimulation. Based on the observed up-regulation of SEF measurements during and immediately after pulsed orocutaneous stimulation, it is presumed that the frequency of electrocortical activity is influenced by trigeminal-thalamo-cortical input bilaterally. The SEF modulation may reflect a form of long-term adaptation (plasticity) that facilitates increased rates cortical activity for several minutes after the stimulus is removed.

The pulsed orocutaneous stimulus delivered to the mechanoreceptor-rich oral apparatus of the preterm infant (e.g., patient) appears to have ecological validity as a salient sensory input, which also provides a safe and comforting experience for the infant. Early experiences, such as incorporating gentle approach to care, light dimming, rest periods, flexed position with appropriate support, and kangaroo care, positively alters brain structure and function, including EEG spectral coherence and neurobehavioral functioning. Somatosensory stimulation plays an important role in brain function and psychomotor development, and is suggested to minimize the risk of developmental disorders among preterm infants. Massage has been shown to be very beneficial to premature infants. Massage applied to the chest, arms, abdomen, legs, back, and face produced an increase in aEEG amplitudes and significantly increased the dominant frequency of $\delta$, $\alpha$, $\theta$, and $\beta$ waves in the EEG. The utility of spectral EEG measures is also apparent in somatosensory stimulation interventions. For example, skin-to-skin contact accelerates brain maturation in healthy preterm infants resulting in fewer REMs, more quiet sleep, respiratory regularity, longer cycles, and less spectral $\beta$-wave activity.

In step 306, the neural analysis and treatment application 104 generates reports that may be used for diagnosing one or more conditions of the patient. In one embodiment, the application 104 determines a level of asymmetry of the aEEG/rEEG information. A challenge in developmental neuroscience is obtaining a complete understanding of structural and functional hemispheric asymmetries in early life. A significant asymmetry in cortical SEF measurements during oral somatosensory stimulation among preterm infants recorded at 32 weeks PMA has been seen. Indeed, there is an abundance of experimental evidence to support anatomic and functional cortical asymmetry in early life to account for SEF asymmetry. Macroscopic left-right differences has been shown to be present from the fetal life and onward. The developmental time scale may also differ between the cerebral hemispheres. Post-mortem studies have shown that the superior frontal gyrus, the superior temporal gyrus, and Heschl's gyrus appear 1 to 2 weeks sooner in the right hemisphere than in the left, whereas other evidence has shown that the plenum temporal and Heschl's gyrus are larger in the left hemisphere in fetuses and infants. Gray and white matter volumes in neonates tend to be larger in the left hemisphere, which is opposite that in adults. An early rightward morphological asymmetry in the fetal brain during the third trimester, and a right temporal sulcus larger than the left has also been reported. Myelination asymmetries have been observed in infants 3 to 11 months of age with white matter in the right cerebellum/left cerebrum exhibiting slower myelination relative to the left cerebellum/right cerebrum. DTI and spatial localization methods have been used to demonstrate early leftward symmetries in the arcuate fasciculus and corticospinal tract. These results suggest that the early macroscopic geometry, microscopic organization, and maturation of these white matter bundles are related to later functional lateralization. Among the most intriguing lateralized functions in humans are hand preference and speech-language function. Preterm infants born more than 30 weeks gestational age (GA) exhibit hemispheric asymmetry at 35 weeks post-conceptional age in the form of right lateralization for functional pitch processing, including both signal detection and discrimination.

In step 308, the neural analysis and treatment application 104 develops a therapeutic plan for the patient. In one embodiment, the application 104 develops a therapeutic plan to provide cortical adaptation for the patient 110. Adaptation as used herein refers to response attenuation in response to repeated stimulation. Adaptation has many forms (short-term and long-term) and is apparent in the periphery at the mechanosensitive nerve ending, within spinal cord, brainstem, and thalamic subnuclei, and finally among vast arrays of local circuits within the primary (S1) and secondary (S2) somatosensory cortices. Cortical adaptation to sustained sensory input is regarded as one of the most ubiquitous forms of short-term plasticity. In humans, this mechanism helps to improve our spatial and temporal resolution of sensory events, which in turn nurtures motor learning and aids in the development of categorical perception for higher cognitive and communicative function. Neural adaptation can be observed in either the amplitude or frequency domain. In terms of frequency-following capabilities, the rate of neural response adaptation tends to increase as one proceeds from the periphery to the S1/S2 cortex. For example, using the same pulsed pneumatic orocutaneous stimulus with a Soothie® silicone pacifier provide cortical adaptation in neuromagnetic response magnitude in S1 and S2 in young adults.

A significant after-effect or persistence in SEF adaptation was observed in the preterm infants who received the pulsed orocutaneous stimulation. Use of a controlled somatosensory inputs reveal the emergence of cortical adaptation may serve as a biomarker of brain maturation. In the mature brain, sustained sensory stimulation leads to transformations in the thalamocortical encoding that impact the nature of information conveyed about the sensory stimuli. Changes in mid-layer cortical neuron spiking activity reflect a switch in their role with adaptation, from coincidence detectors (tuned for stimulus detection in a non-adapted state) to integrators (tuned for stimulus discrimination after adaptation). With repetitive stimulation, a dynamic cortical inhibitory mechanism shapes the initial activity into a stimulus-specific spatial pattern of columnar assemblies. Lateral interactions between adjacent columns are the result of intrinsic inhibitory (GABA-ergic) and excitatory effects (glutamate) which lead to a differential modification (across columns) of the membrane potential that can last for as long as several seconds.

The process described above continues throughout operation of the neural analysis and treatment system 100. However, when use of the neural analysis and treatment system 100 is no longer needed or desired the process ends.

EXAMPLE OF USE:

Study infants were randomly assigned to two groups, including those who received pulsed orocutaneous stimulation (Treatment group), and those who did not (Control group). The participants included 22 healthy preterm infants (16M/6F), with a mean GA of 28.56 wks (SD=2.06), birthweight of 1229.8 gms (SD=338.40), and PMA of 32.17 wks (SD=1.09) at the time of testing. Parents were consented in accordance with the Santa Clara Valley Medical Center Human Subjects Institutional Review Board approval. Inclusion criteria included those infants having a gestational age of 24-32 weeks, and at least 28 weeks post-menstrual age at the time of enrollment. Exclusion criteria included those infants having chromosomal abnormalities, multiple congenital anomalies, or any major congenital anomalies. Infants with history of severe IVH, necrotizing enterocolitis (e.g., greater than stage III), vocal cord paralysis, seizures, and meningitis, or nippling all feeds at the time of enrollment.

The primary goal was to determine the effects of highly controlled (pneumatic servo) pulsed orocutaneous stimulation presented during gavage feedings begun at 32 weeks PMA on the modulation of aEEG/rEEG activity in the amplitude domain among medically stable preterm infants monitored in the neonatal intensive care unit (NICU).

The stimulation was delivered by a servo-controlled pneumatic amplifier (NTrainer System®, Innara Health™, Shawnee, Kans. USA) specially designed to transmit repeating pneumatic pulse trains to the soft tissues of the infant's lips-anterior tongue-intraoral mucosa-jaw through a regular (green) Soothie™ silicone pacifier. This 6-cycle orocutaneous stimulus burst was frequency modulated, consisting of sequential cycle periods of 510, 526, 551, 580, and 626 milliseconds with an intertrain interval of 2 seconds.

Figure 4:
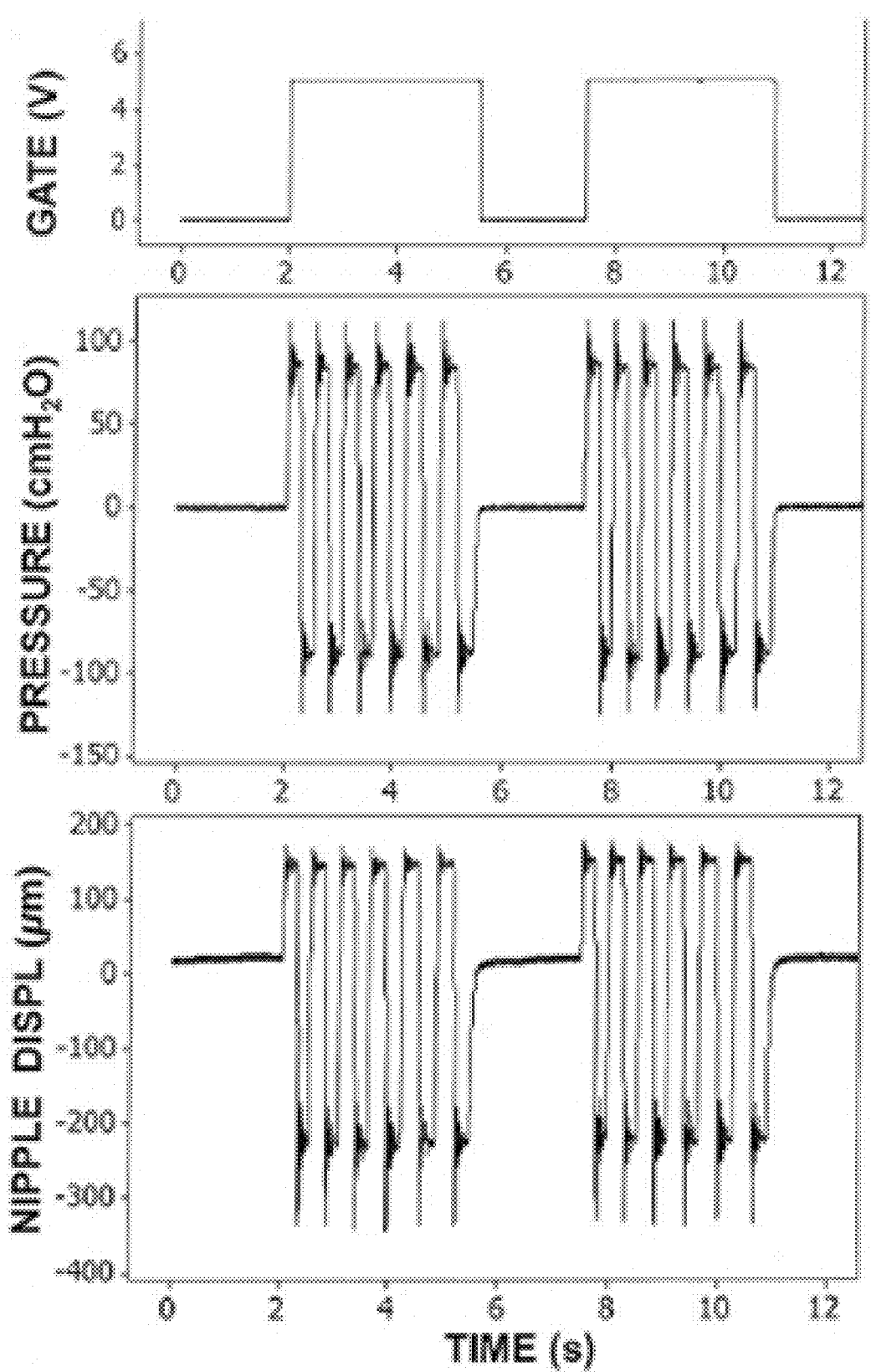
FIG. 4 illustrates example frequency modulated (FM) somatosensory stimulus bursts as presented to the preterm infants through a pneumatically-charged silicone pacifier according to one aspect of the present disclosure.

FIG. 4 illustrates example frequency modulated (FM) somatosensory stimulus bursts as presented to the preterm infants through a pneumatically-charged silicone pacifier. Each burst consists of 6 pulses followed by a 2-second pause period. A servo-controlled microprocessor provides the gating function (top panel) to dynamically 'charge' the intraluminal pressure of the silicone pacifier (middle panel) resulting in rapid conformational changes in pacifier geometry (bottom panel). The peak-to-peak displacements associated with these pneumatically charged transitions in the intraluminal pressure is approximately 400 microns with a 10-90% rise/fall time of 31 milliseconds.

The spatiotemporal features of this somatosensory stimulus mimics the synchronous volleys of afference associated with ororhythmic patterning, and thus constitutes an approximation to a physiologically salient somatosensory experience normally encoded by the trigeminal system. The pressure rise-fall time (10-90% intercepts) of each 50 millisecond pulse was 31 milliseconds, and the resultant displacement at the pacifier-lip/tongue tissue interface was approximately 400 microns. Three-minute pneumatic orocutaneous stimulation periods were interleaved with 5.5 minute pause periods, where the pacifier was removed from the infant's mouth.

Figures 5, 6:
FIG. 5 illustrates an example orocutaneous stimulation schedule that results from the test according to one aspect of the present disclosure.
FIG. 6 illustrates an example preterm infant with aEEG and pneumatically pulsed stimulation through a regular Philips AVENT BPA-free Soothie silicone pacifier coupled to the digitally-controlled handpiece of the NNS system according to one aspect of the present disclosure.

FIG. 5 illustrates an example orocutaneous stimulation schedule that results from the test. Nine sequential data blocks are indicated by P1 through P9 spanning 32 minutes. The pulsed orocutaneous stimulus (NT Stimulus) or the blind 'sham' pacifier are presented to the infant during periods P3, P5, and P7. The pacifier apparatus was removed from the baby's mouth during periods P1, P2, P4, P6, P8, and P9.

The control infants received a sham stimulation program in which infants were offered the same type of Soothie pacifier without patterned stimulation (blind pacifier). The staging of a single stimulation session was given concurrently with gavage (e.g., tube-feeding). Up to three such sessions were administered to preterm infants per day according to their 3-hour feed cycles. Infants were swaddled with limbs at midline, and in a quiet-awake to drowsy state during stimulation.

For EEG recording and signal processing, four neonatal hydrogel sensors were placed in the C3, C4, P3, and P4 positions according to the international 10-20 system for EEG monitoring. Acceptable electrode impedance was less than 10 kiloohm (k$\Omega$). EEG signals were recorded on a BRM3 monitor for up to 4-days beginning at approximately 32 weeks PMA. FIG. 6 illustrates an example preterm infant with aEEG and pneumatically pulsed stimulation through a regular Philips AVENT BPA-free Soothie silicone pacifier coupled to the digitally-controlled handpiece of the NTrainer System®. EEG signals derived from hydrogel electrodes placed at C3-P3 and C4-P4 were recorded on a bedside aEEG monitor.

The right- and left-side EEG signals were amplified by a factor of approximately five thousand and bandpass-filtered (e.g., first-order high-pass filter at (f, −3 dB @ 1 Hz) and a fourth-order low-pass Butterworth at (f, −3 dB @ 50 Hz)), and digitized at a sampling rate of 256 Hz. Brainz Analyze Research (v1.5) software was used to derive the aEEG maxima/mean/minima, and rEEG amplitude bands (A [0-10 microvolts], B [10-25 microvolts], C [25-50 microvolts], D [50-100 microvolts], and E [>100 microvolts]) at 1-min intervals. These EEG measures were derived from 9 sequential epochs (data blocks), spanning 32 minutes each, and centered over the pneumatic orocutaneous or the blind pacifier 'sham' stimulus conditions. A total of 1620 EEG blocks were analyzed among the 22 infants. The average number of orosensory sessions sampled per infant was 8.18 (SE=1.09). Portions of recordings were excluded from analysis if electrode impedance exceeded 10 k$\Omega$, or if there was the presence of movement, electrical noise artifact, or asymmetry of voltage in one channel.

For statistical analysis, mixed models for repeated measures were used to compare the aEEG and rEEG amplitude measures between four stimulus conditions, including (1) NT 'ON' pacifier+pneumatic pulse, (2) NT 'ON' control epochs, (3) NT 'OFF' blind 'sham' pacifier, and (4) NT 'OFF' control epochs. Adjusting for the infants' gestational ages and birth weights, mixed models estimated the stimulus effect on each outcome via the use of restricted maximum likelihood estimator and compound symmetric error covariance structure. When the stimulus effect was significant at 0.05 alpha level, pair-wise comparisons of adjusted means were performed using a Bonferroni-corrected p-value. All analyses were conducted using SAS 9.3.

Figure 7:
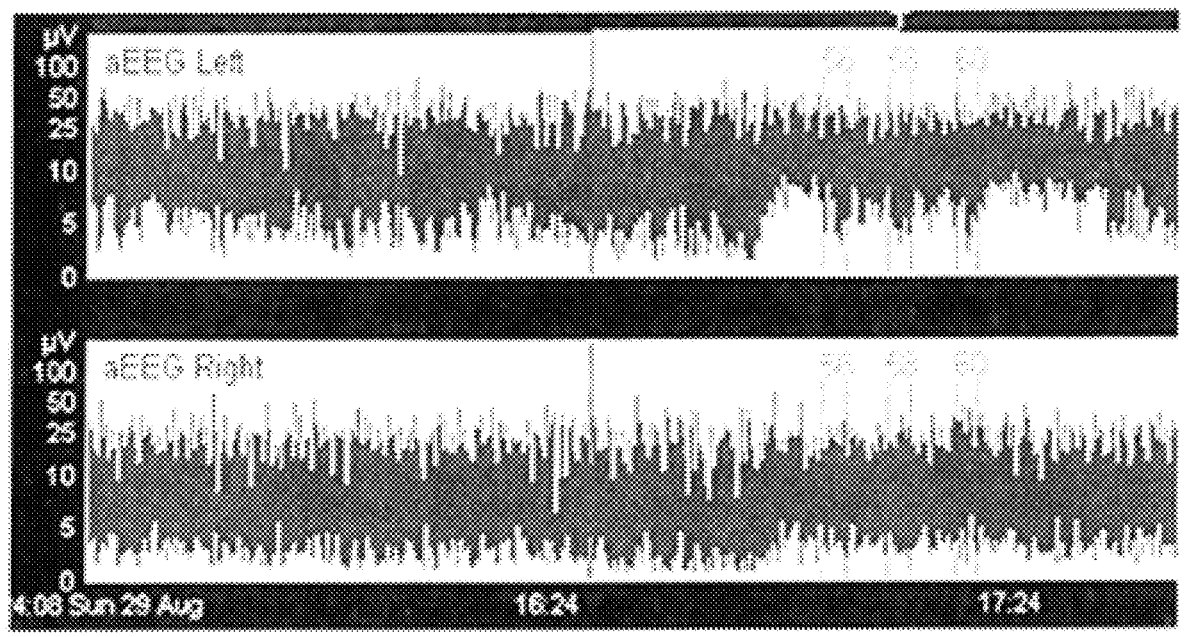
FIG. 7 illustrates example bi-hemispheric aEEG sampled from C3-P3 and C4-P4 on a preterm infant according to one aspect of the present disclosure.

Regarding the measured aEEG amplitude, the presence of the patterned pneumatic orocutaneous stimulation, and its aftereffects produced a significant reorganization of the EEG recorded from the left and right hemisphere in preterm infants as reflected in aEEG and rEEG amplitude parameters. An example of the bi-hemispheric aEEG sampled from C3-P3 and C4-P4 on a preterm infant (32 weeks PMA). FIG. 7 illustrates example bi-hemispheric aEEG sampled from C3-P3 and C4-P4 on a preterm infant (32 wks PMA). Indexed events (#56, 58, and 60) represent the onset of 3-minute pulsed orocutaneous stimulation periods interleaved with 5.5 minute no-stimulus periods. As shown, aEEG amplitude modulation is present in the electrophysiological record during somatosensory stimulation. Indexed events at 56, 58, and 60 represent the onset of 3-minute pulsed orocutaneous stimulation periods interleaved with 5.5 minute no-stimulus periods. During pulsed somatosensory stimulation, aEEG modulation at the lower and upper amplitude margins of the electrophysiological record was also present.

In the aEEG domain, stimulus condition yielded significant main effects for aEEG maxima, mean, and minima in the left hemisphere ($p<0.0001$), and significant main effects for aEEG maxima and mean in the right hemisphere. Stimulus condition was also a significant main effect for the crosshead measures of aEEG maxima and mean. Cortical response asymmetry during patterned orocutaneous stimulation was apparent, with the largest changes in aEEG amplitude measures occurring in the left hemisphere. For example, the blind pacifier condition yielded an average aEEG maxima in left and right hemisphere of 12.89 microvolts and 12.81 microvolts, respectively, whereas the addition of the patterned orocutaneous stimulation yielded an average aEEG maxima of 11.68 microvolts and 13.38 microvolts, respectively ($p<0.001$). Based on the individual hemispheric and crosshead measures, the presence of the pulsatile oral somatosensory stimulation, distinct from a blind pacifier alone, alters the balance in excitation with significant attenuation of the aEEG in the left hemisphere and facilitation in the right hemisphere. This translates to an interhemispheric difference of 1.7 microvolts during pulsatile oral somatosensory stimulation and only 0.08 microvolts in the presence of a blind pacifier ($p<0.001$). Behaviorally, the orocutaneous stimulation had a calming effect for preterm infants who began the stimulation period in the quiet-alert state and often transitioned to a drowsy-sleep state.

Figure 8:
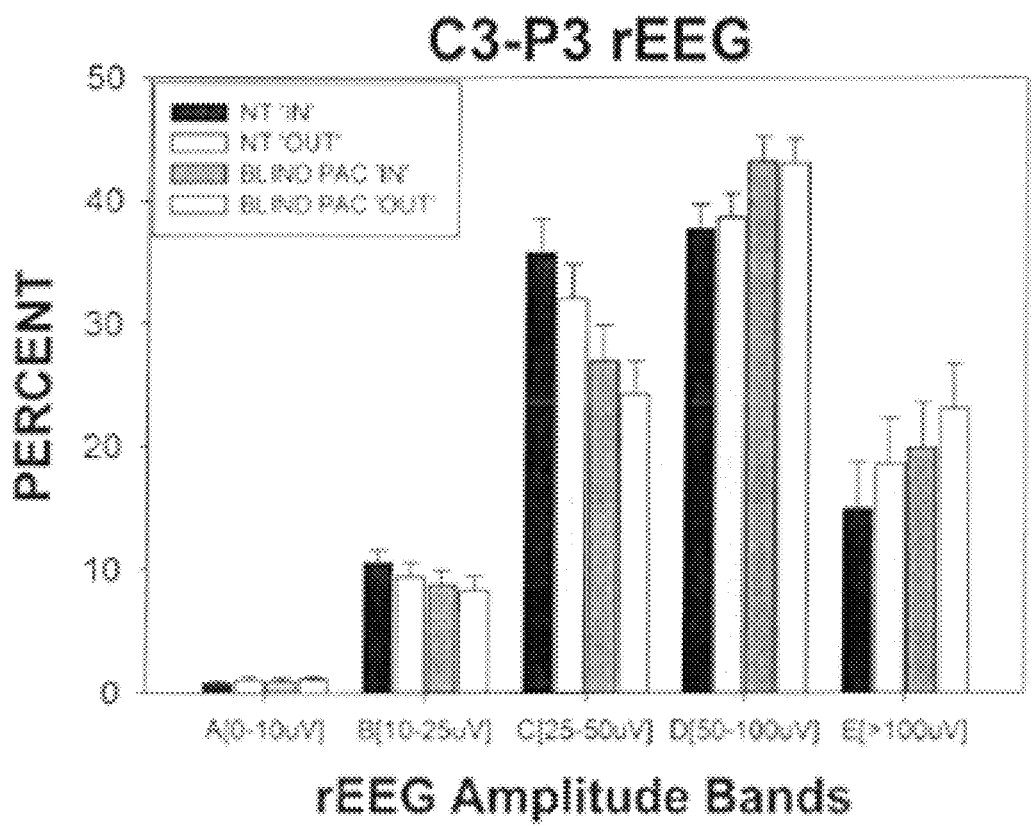
FIG. 8 illustrates example rEEG amplitude bands derived from the left hemisphere EEG (C3-P3) in preterm infants during pulsed orocutaneous and blind pacifier stimulation conditions according to one aspect of the present disclosure.
Figure 9:
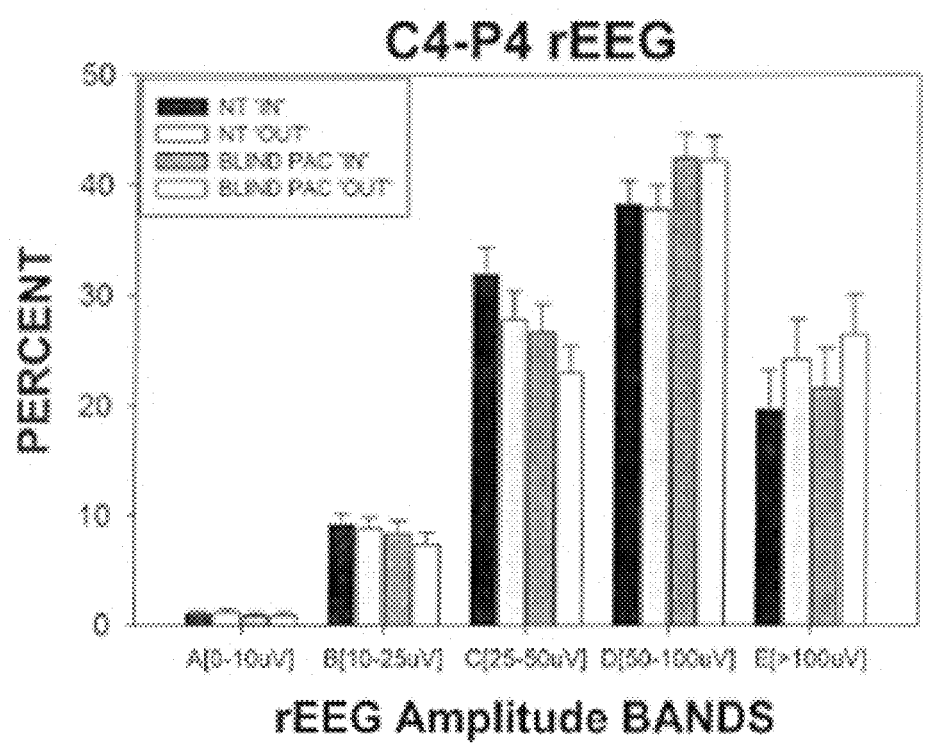
FIG. 9 illustrates example rEEG amplitude bands derived from the right hemisphere EEG (C4-P4) in preterm infants during pulsed orocutaneous and blind pacifier stimulation conditions according to one aspect of the present disclosure.
Figure 10A:
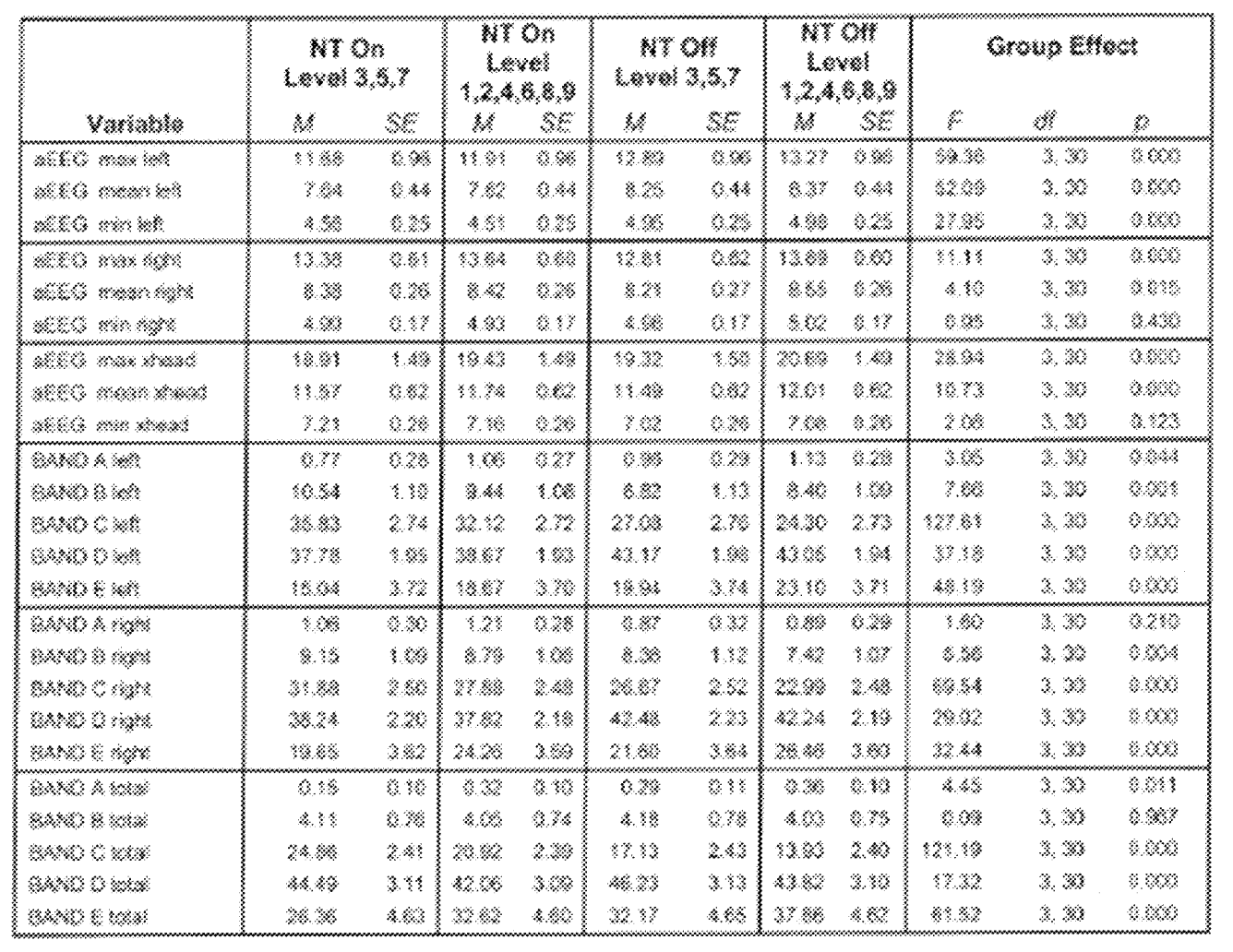

Regarding the rEEG amplitude bands, the presence of the patterned pneumatic orocutaneous stimulation produced a significant reorganization of rEEG amplitude bands in both hemispheres. FIG. 8 illustrates example rEEG amplitude bands sampled from the left hemisphere (C3-P3) in preterm infants during pulsed orocutaneous and blind pacifier stimulation conditions. NT 'IN' indicates the pneumatically charged pacifier is in the mouth, NT 'OUT' indicates the charged pacifier is out of the mouth, BLIND PAC 'IN' indicates the regular Soothie pacifier is in the mouth, and BLIND PAC 'OUT' indicates the regular Soothie pacifier is out of the baby's mouth. Statistically significant main and pair-wise comparison effects are summarized in Tables 2 and 3. FIG. 9 illustrates example rEEG amplitude bands sampled from the right hemisphere (C4-P4) in preterm infants during pulsed orocutaneous and blind pacifier stimulation conditions. NT 'IN' indicates the pneumatically charged pacifier is in the mouth, NT 'OUT' indicates the charged pacifier is out of the mouth, BLIND PAC 'IN' indicates the regular Soothie pacifier is in the mouth, and BLIND PAC 'OUT' indicates the regular Soothie pacifier is out of the baby's mouth. Statistically significant main and pair-wise comparison effects are summarized in FIGS. 10A and 10B, which illustrate mixed model adjusted means, and Post-hoc pair-wise comparison. G1: NT 'On' and Level 3,5,7; G2: NT 'On' and Level 1,2,4,6,8,9; G3: NT 'Off' and Level 3,5,7; and G4: NT 'Off' and Level 1,2,4,5,8,9, respectively.

Overall, significant proportions of the rEEG shifted from the E and D bands to the C band, with considerably less change observed at the low end of rEEG voltage, including bands A and B. Asymmetry was also observed with the degree of reorganization greater in the left hemisphere.

Figure 11:
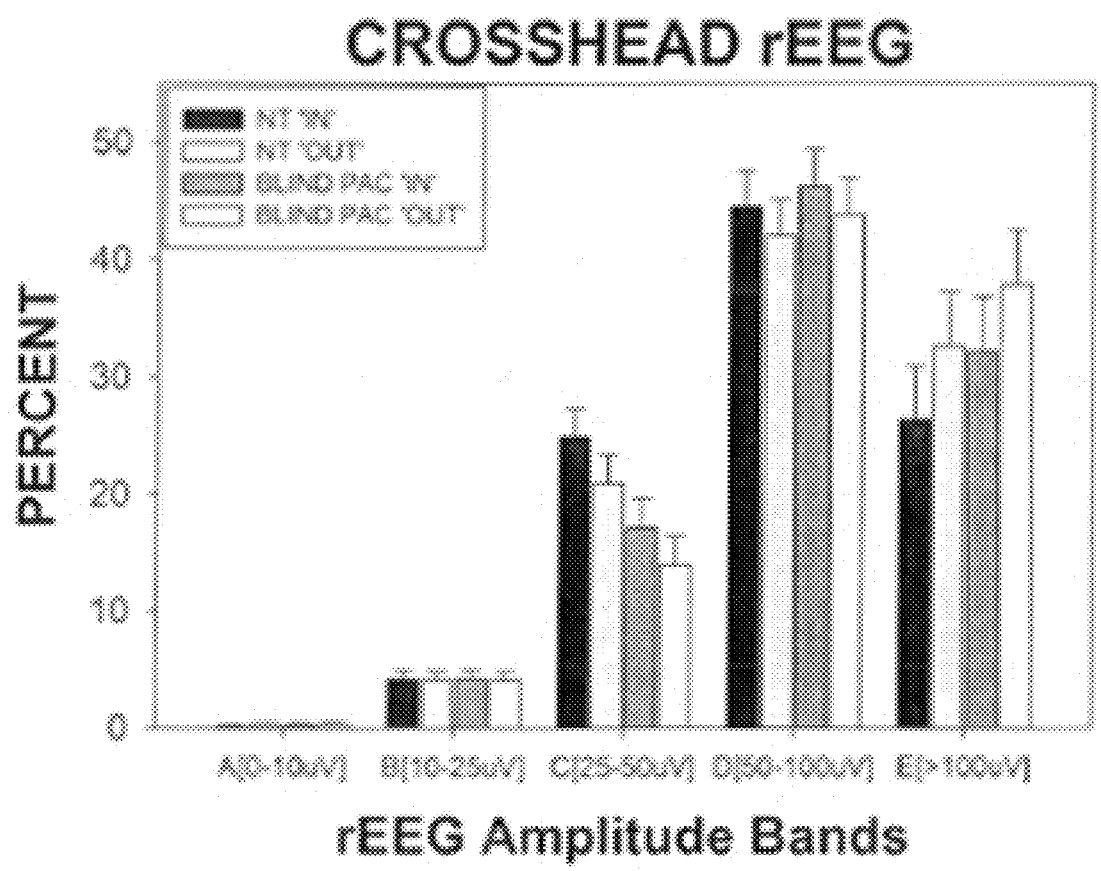
FIG. 11 illustrates example rEEG amplitude bands derived from the crosshead EEG montage (P3-P4) in preterm infants during pulsed orocutaneous and blind pacifier stimulation conditions according to one aspect of the present disclosure.

FIG. 11 illustrates example rEEG amplitude bands sampled from the crosshead montage (P3-P4) in preterm infants during pulsed orocutaneous and blind pacifier stimulation conditions. NT 'IN' indicates the pneumatically charged pacifier is in the mouth, NT 'OUT' indicates the pneumatically-charged pacifier is out of the mouth, BLIND PAC 'IN' indicates the regular Soothie pacifier is in the mouth, and BLIND PAC 'OUT' indicates the regular Soothie pacifier is out of the baby's mouth. As shown in FIG. 11, stimulus condition yielded significant main effects for crosshead amplitude bands A (0-10 microvolts, $p=0.011$), C (25-50 microvolts, $p<0.0001$), D (50-100 microvolts, $p<0.0001$), and E (>100 microvolts, $p<0.0001$). The proportion of rEEG adjusted means in the E and C bands for the blind pacifier condition was 32.17% and 17.13%, respectively. Preterm infants who received the pulsatile orocutaneous stimulation manifest a significant shift in rEEG power from the E band (−26.36%) to the C band (+24.86%). A persistence or 'after-effect' in the reorganization of the rEEG power banding was observed during the 5.5-minute no-stimulus epochs that followed each of the 3-minute orocutaneous stimulation periods. This after-effect was also significantly different between the blind pacifier and pulsatile oral somatosensory stimulation condition ($p<0.0001$). A detailed listing of pair-wise comparisons of adjusted means is given in FIG. 10B. Thus, the 3-minute pulsed somatosensory stimulation epochs served to enhance rEEG band C activity while suppressing higher voltage in rEEG bands D and E. Preterm infants exposed to the pulsed orocutaneous stimulation yielded a greater proportion of band C activity throughout the 23-minute recording period that followed the first stimulus block when compared to the blind pacifier condition.

Figure 12:
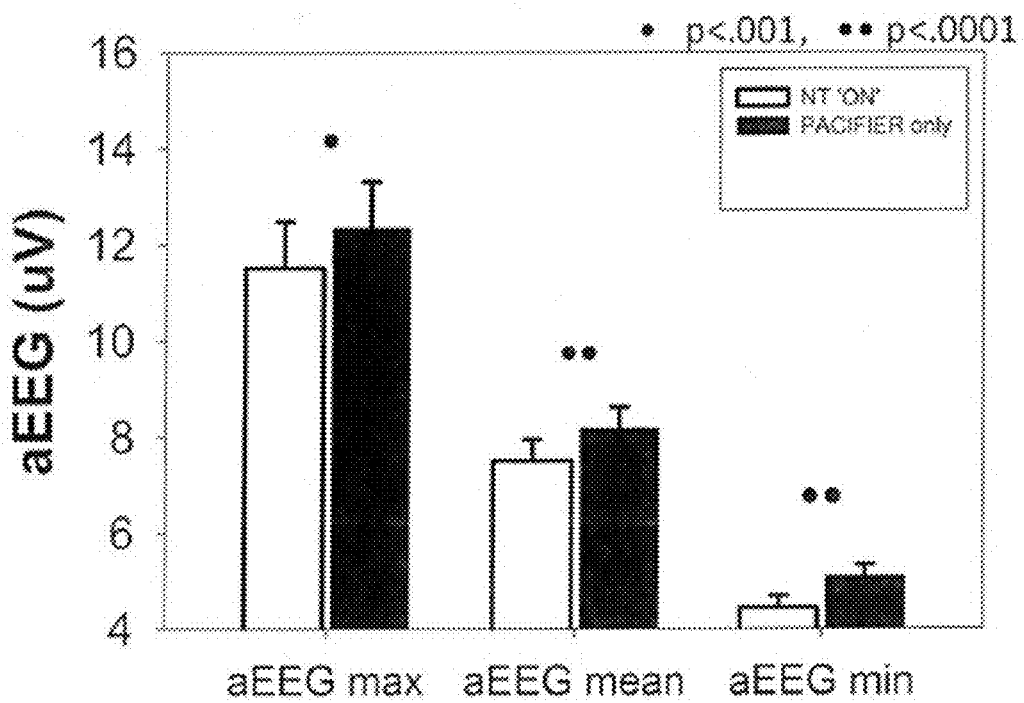
FIG. 12 is a chart illustrating aEEG data (maxima, mean, and minima) sampled from the left hemisphere (C3-P3) in preterm infants during pulsed orocutaneous (NT 'ON') and blind pacifier (PACIFIER only) stimulation conditions.

FIG. 12 illustrates Mean aEEG measures (maxima, mean, and minima) sampled from the left hemisphere (C3-P3) in preterm infants during pulsed orocutaneous (NT 'ON') and blind pacifier (PACIFIER only) stimulation conditions.

Figure 13:
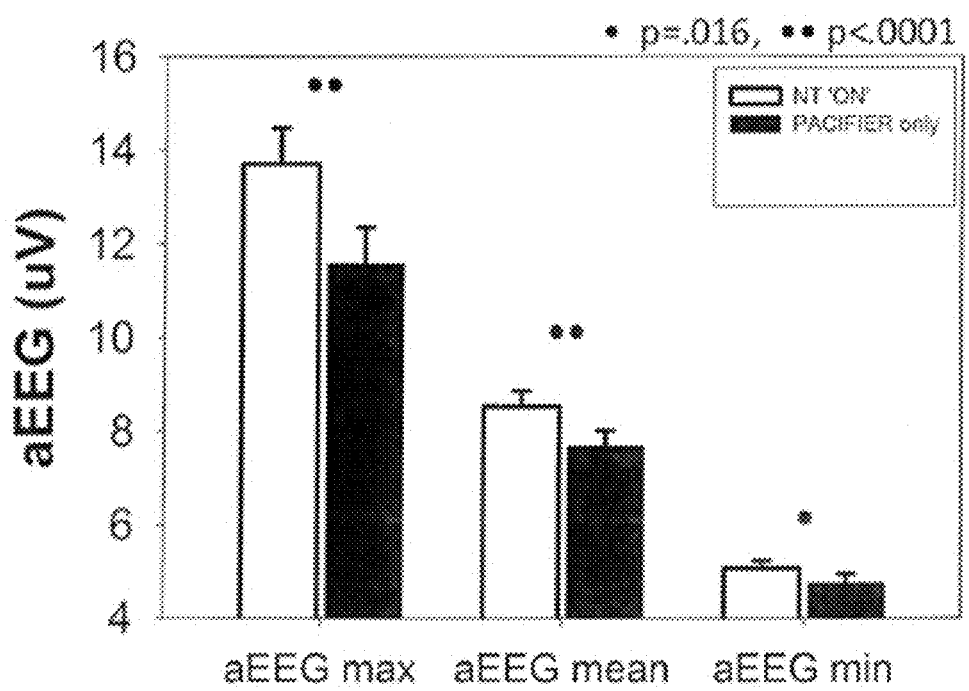
FIG. 13 is a chart illustrating aEEG data (maxima, mean, and minima) sampled from the right hemisphere (C4-P4) in preterm infants during pulsed orocutaneous (NT 'ON') and blind pacifier (PACIFIER only) stimulation conditions.

FIG. 13 illustrates Mean aEEG measures (maxima, mean, and minima) sampled from the right hemisphere (C4-P4) in preterm infants during pulsed orocutaneous (NT 'ON') and blind pacifier (PACIFIER only) stimulation conditions.

Those skilled in the art will appreciate that variations from the specific embodiments disclosed above are contemplated by the invention. The invention should not be restricted to the above embodiments, but should be measured by the following claims.

What is claimed is:

1. A neural analysis and treatment system comprising:
   a computing device having at least one non-transitory local memory and at least one processor, the at least one non-transitory local memory comprising computer executable instructions executed by the at least one processor to:
   receive, by the at least one processor, electroencephalography (EEG) data comprising amplitude-integrated electroencephalography (aEEG) and range-EEG (rEEG) measurements from one or more electrodes associated with a patient exposed to somatosensory stimulation;
   generate spectral edge frequency (SEF) information from the received EEG data;
   determine one or more neural characteristic of the patient using the SEF information, wherein the one or more neural characteristic comprises variance in voltages of the received EEG data, continuity of the received EEG data, or sleep-wake cycling of the patient; and
   develop one or more therapeutic plans based upon the one or more neural characteristic of the patient, wherein the one or more therapeutic plans entrain a brain activity for controlling respiration and mastication in a patient, wherein the patient is a preterm infant or a post-conceptional age infant.

2. The system of claim 1, wherein the SEF information comprises at least one of an SEF modulation of an EEG spectra of the received EEG data or an SEF asymmetry of the EEG spectra.

3. The system of claim 2, wherein the SEF information is derived from an rEEG modulation of the patient.

4. The system of claim 2, wherein the SEF information is derived from an rEEG asymmetry of the patient.

5. The system of claim 2, wherein the SEF information is derived from an aEEG modulation of the patient.

6. The system of claim 2, wherein the SEF information is derived from an aEEG asymmetry of the patient.

7. The system of claim 1, wherein the one or more neural characteristic is determined using an SEF asymmetry of the patient.

8. The system of claim 1, wherein the one or more neural characteristic comprises a cortical activity of the patient.

9. The system of claim 1, further comprising the processor being configured to:
   generate a signal, received at an entrainment device to perform the one or more therapeutic plans on the patient;
   receive, by the processor, other EEG data from one or more electrodes associated with the patient, after the one or more therapeutic plans have been performed;
   generate additional SEF information from the other received EEG data;
   determine at least one other neural characteristic of the patient according to the additional SEF information; and
   determine a brain development level of the patient according to the one or more neural characteristic and the at least one other neural characteristic.

10. The system of claim 9, wherein the brain development level comprises a quantified cortical adaptation of the patient.

11. The system of claim 9, wherein the additional SEF information comprises at least one of an SEF modulation of the other received EEG or an SEF asymmetry of the other received EEG data.

12. The system of claim 11, wherein the additional SEF information is derived from an rEEG modulation of the patient.

13. The system of claim 11, wherein the additional SEF information is derived from an rEEG asymmetry of the patient.

14. The system of claim 11, the additional SEF information is derived from an aEEG modulation of the patient.

15. The system of claim 11, the additional SEF information is derived from an aEEG asymmetry of the patient.

16. The system of claim 9, wherein the at least one other neural characteristic comprises a cortical activity of the patient.

17. The system of claim 9, further comprising the processor being configured to generate one or more reports that include at least one of the one or more neural characteristics, the at least one other neural characteristic, and the brain development level of the patient.

18. A method for neural analysis and treatment plan development for providing neurological entrainment to a patient, using a computing device having at least one processor and at least one non-transitory local memory further comprising computer executable instructions executed by the at least one processor, the method comprising:

at the computing device:
receiving electroencephalography (EEG) data comprising amplitude-integrated electroencephalography (aEEG) and range-EEG (rEEG) measurements from one or more electrodes associated with the patient exposed to somatosensory stimulation;
generating spectral edge frequency (SEF) information from the received EEG data;
determining one or more neural characteristic of the patient using the SEF information wherein the one or more neural characteristic comprises variance in voltages of the received EEG data, continuity of the received EEG data, or sleep-wake cycling of the patient;
developing one or more therapeutic plans based upon the one or more neural characteristic of the patient, wherein the one or more therapeutic plans entrain a brain activity for controlling respiration and mastication in the patient, wherein the patient is a preterm infant or a post-conceptional age infant.

19. The method of claim 18 further comprising:
using an entrainment device to perform the one or more therapeutic plans on the patient;
receiving, at the computing device, other EEG data from one or more electrodes associated with the patient, after the one or more therapeutic plans have been performed;
generating, at the computing device, other SEF information from the other received EEG data;
determining, at the computing device, another neural characteristic of the patient according to the other SEF information; and
determining, at the computing device, a brain development level of the patient according to the one or more neural characteristic and the other neural characteristic.

20. The method of claim 19, wherein the brain development level comprises a quantified cortical adaptation of the patient.

21. The method of claim 19, wherein at least one of the one or more neural characteristic or other neural characteristic comprises an SEF modulation of the patient.

22. The method of claim 19, wherein at least one of the one or more neural characteristic or other neural characteristic comprises a rEEG modulation of the patient.

23. The method of claim 19, wherein at least one of the one or more neural characteristic or other neural characteristic comprises a rEEG asymmetry of the patient.

24. The method of claim 19, wherein at least one of the one or more neural characteristic or other neural characteristic comprises an aEEG modulation of the patient.

25. The method of claim 19, wherein at least one of the one or more neural characteristic or other neural characteristic comprises an aEEG asymmetry of the patient.

26. The method of claim 19, wherein at least one of the one or more neural characteristic or other neural characteristic comprises an SEF asymmetry of the patient.

27. The method of claim 19, wherein at least one of the one or more neural characteristic or other neural characteristic comprises a cortical activity of the patient.

* * * * *